United States Patent [19]
Davankov et al.

[11] Patent Number: 6,156,851
[45] Date of Patent: Dec. 5, 2000

[54] MATERIAL FOR PURIFICATION OF PHYSIOLOGICAL LIQUIDS OF ORGANISM

[75] Inventors: Vadim Davankov; Maria Tsyurupa; Ludmila Pavlova, all of Moscow, Russian Federation

[73] Assignee: Renal Tech International LLC, New York, N.Y.

[21] Appl. No.: 09/366,047

[22] Filed: Aug. 2, 1999

Related U.S. Application Data

[62] Division of application No. 09/019,583, Feb. 6, 1998.

[51] Int. Cl.⁷ .................... C08C 19/12; C08C 136/20; C08C 19/24; B32B 3/26; B32B 9/00
[52] U.S. Cl. .................... 525/332.2; 428/304.4; 428/318.4; 525/332.7; 525/333.3; 525/340
[58] Field of Search .............. 428/304.4, 318.4; 502/402; 525/332.2, 332.7, 333.3, 340

[56] References Cited

U.S. PATENT DOCUMENTS

| | | | |
|---|---|---|---|
| 4,140,652 | 2/1979 | Korshak et al. | 252/426 |
| 4,500,652 | 2/1985 | Misaka et al. | 521/33 |
| 4,950,332 | 8/1990 | Stringfield et al. | 127/55 |
| 5,151,192 | 9/1992 | Matkovich et al. | 210/646 |
| 5,773,384 | 6/1998 | Davankov et al. | 502/402 |
| 5,904,663 | 5/1999 | Braverman et al. | 604/5 |

*Primary Examiner*—David Wu
*Assistant Examiner*—Tanya Zalukaeva
*Attorney, Agent, or Firm*—I. Zborovsky

[57] ABSTRACT

Purification of physiological liquids of organism is performed by passing a physiological liquid with toxicants removed from a patient through a material which has a size a shape, and a structure selected so as to remove toxic compounds in the molecular range of 300 to 30000 Dalton from the physiological liquid and which is composed of a porous hydrophobic divinylbenzene copolymer which initially has surface exposed vinyl groups in which thereafter the vinyl groups are chemically modified so as to form different surface exposed functional groups with a greater hydrophilicity and greater biocompatibility than those of the vinyl groups.

2 Claims, No Drawings

MATERIAL FOR PURIFICATION OF PHYSIOLOGICAL LIQUIDS OF ORGANISM

CROSS REFERENCE TO A RELATED APPLICATION

This application is a division of application Ser. No. 09/019,583 filed on Feb. 6, 1998.

BACKGROUND OF THE INVENTION

The present invention relates to material for purification of physiological liquids of organism.

It is well known that physiological liquids of organisms such as blood, plasma, peritoneal liquid etc., accumulate and transport various toxicants in the case of poisoning the organism as well as in the case of diseases, in particular diseases of liver and kidneys. It is therefore advisable to remove the toxicants from the physiological liquids to significantly improve the situation of the patient. A plurality of methods have been invented and have been utilized for removing toxicants from blood, plasma and other physiological liquids. One of the most efficient methods is hemodialysis. This method, however, is generally restricted to removing small toxic molecules, whereas toxins belonging to the so-called middle-size molecules (between 500 and 30000 Dalton molecular weight) are eliminated too slowly, even with modern "high flux" dialyser membranes. It is believed to be advisable to further improve the existing methods so as to provide an efficient purification of the physiological liquid of organism, especially with respect to above toxicants having larger molecular sizes, for the purpose of preventing propagation of diseases or curing the disease.

According to the present invention, a wider spectrum of toxic compounds should be removable from blood or other physiological fluids, if conventional hemodialysis procedure is supplemented with an adsorption procedure. The latter should be responsible for removing larger toxins which diffusion through the membrane of the dialyser is too slow.

The adsorbing material should both exhibit high adsorption capacity toward toxins in the middle range of molecular weights and disply sufficient compatibility with blood or the corresponding physiological fluid. Designing suitable polymeric adsorbing material is one of the aims of present invention.

Macroporous styrene-divinylbenzene copolymers represents the most popular type of polymeric adsorbing materials. Many companies manufacture adsorbents of this category. Amberlite XAD-4 (by Rohm and Haas) being probably the best known one. Equally interesting, though less abandoned, are macroporous adsorbing materials manufactured by copolymerization of divinylbenzene (DVB) with other monomers, i.g., buthyl methacrylate, acrylo nitrile and others.

In order to maintain the porous architecture and nearly constant volume of polymeric particles under various conditions of usage, the three-dimensional network of these polymers has to be sufficiently rigid, i.e., it must contain a high proportion of crosslinking divinylbenzene. The latter product, when in pure state, is rather expensive. The more available technical product contains up to 30–40% of ethylvinyl styrene, so that commercially available macroporous adsorbents should be better referred to as copolymers of DVB, ethylvinyl styrene and styrene. Usually, this monomer mixture is provided with organic solvents serving as the diluters which cause a micro phase separation during the polymerization procedure and thus resulting in the macroporous structure of the final material.

It has been shown repeatedly that the radical polymerization procedure does never consume all the vinyl groups of DVB introduced into copolymerization. On the average, about 30% of DVB species fail to serve as crosslinking bridges and remain involved into the network with only one of its two vinyl groups. The presence of a relatively high amount of pending vinyl groups is therefore a characteristic feature of the macroporous adsorbents. It can be expected that these free vinyl groups are preferably exposed to the surface of the polymer beads and their macropores and should be readily available to chemical modification.

The chemical modification of the surface of macroporous DVB-copolymers relies on chemical reactions of the surface-exposed pendant vinyl groups and aims at converting these groups into more hydrophilic functional groups. This conversion provides the initial hydrophobic adsorbing material with the property of hemocompatibility, since the hydrophilic surfaces adsorb less blood cells and plasma proteins and do not activate the clotting cascades as rapidly as does the initial hydrophobic surface.

Some solutions were disclosed in our earlier patent application Ser. No. 08/756,445.

SUMMARY OF THE INVENTION

Accordingly, it is an object of present invention to provide a material for purification of physiological liquids of organism, which is a further modification in the above specified field.

In accordance with the present invention, the material for purification of physiological liquids of organism is proposed, which is composed of a porous hydrophobic divinylbenzene copolymer which initially has surface exposed vinyl groups in which thereafter the vinyl groups are chemically modified so as to form different surface exposed functional groups with a greater hydrophilicity and greater biocompatibility than those of the vinyl groups.

When the material for purification of physiological liquids of organism is provided in accordance with the applicant's invention, it provides for highly advantageous results.

DESCRIPTION OF PREFERRED EMBODIMENTS

In accordance with the present invention, a purification of physiological liquids of organism by removing toxicants is proposed. A patient's blood is withdrawn from an arterial blood circulatory access point, passed through a material in accordance with the present invention which removes toxicants, and re-enters the patient through a venous access point. Preferably, the material has a size, a shape, and a structure selected so as to remove the toxic compounds in the molecular range of 300 to 30,000 Dalton from the physiological liquid.

The material in accordance with the present invention which is used in the inventive method for purification of physiological liquids of organism and which is produced in accordance with the inventive production method, is a porous hydrophobic divinylbenzene copolymer which initially has surface exposed vinyl groups in which thereafter the vinyl groups are chemically modified so as to form different surface exposed functional groups with a greater hydrophilicity and greater biocompatibility than those of the vinyl groups.

According to the present potential invention, the modification of the surface vinyl groups was made in aqueous or aqueous organic media in the following three principal directions:

grafting hydrophilic polymer chains by a radial polymerization of 2-hydroxyethyl methacrylate, N-vinylpyrrolidone, N-vinylcaprolactam, or other water soluble monomers, oxidation of the vinyl groups to epoxy groups with the subsequent reaction of the epoxy groups with water, ethylene glycol, amines or 2-amonoethanol molecules, and depositing high-molecular-weight hemocompatible polymer, in particular poly(trifluorethoxy) phosphazene onto the surface of the polymeric beads.

In any case the hydrophilic nature of thus modified surfaces could be visualized by the easy wetting of dried modification material with water, whereas the initial dry unmodified adsorbent cannot be wetted by an immediate contact with water.

In the following examples, a mesoporous divinylbenzene-ethylstyrene-styrene copolymer, a typical polystyrene-type adsorbing material and a copolymer of DVB with buthyl methacrylate with surface exposed double bonds were taken for the modification.

The surface-modified materials were shown to exhibit good hemocompatibility, i.e., they did not change noticeably the coagulation time of blood, caused no hemolysis and showed no cytotoxicity effects. When contacted with plasma or whole blood, the materials effectively removed the pool of middle-sized molecules, as could be easily followed by conventional spectrophotometric measurements.

Preparation of Mesoporous Divinylbenzene Copolymers

EXAMPLE 1

A solution of 130 g p-ethylstyrene, 132 g divinylbenzene (a mixture of para and metha-isomers of about 1:1) and 2.62 g benzoyl peroxide in a mixture of 150 ml toluene and 100 ml iso-amyl alcohol was suspended in 4 liters of pure water containing 1% cellulose stabilizer. After 39 min stirring at room temperature, the mixture was heated at 40° C. for 1 hours, 60° C. for 2 hours, 80° C. for 5 hours and 90° C. for 2 hours. After cooling the mixture to room temperature, the beads of the material obtained were filtered and washed with hot water, methanol and water. The polymer was dried in an oven at 80° C. within one day.

EXAMPLE 2

A solution of 75 g buthyl acrylate, 51 g divinylbenzene (a mixture of para and metha-isomers of about 1:1) and 1 g benzoyl in 250 ml of toluene was suspended in 2.4 liters of pure water containing 15 g of cellulose stabilizer at room temperature. After 30 min stirring, the mixture was heated stepwise at 60, 80 and 95° C. within 3 hours for each temperature. After cooling to room temperature, the beads obtained were filtered, washed with hot water, methanol and water. The beads were dried in oven for 7 hours at 80° C.

Grafting Hydrophilic Polymeric Chains to the Surface Exposed Vinyl Groups

EXAMPLE 3

The polymer prepared in Example 1 was washed with ethanol and then rinsed with water, which results in a material fully wetted by water with all its pores filled with water. The material contains 40% polymer and 60% water. To 1 g of the polymer thus wetted with water, 1 ml of 3% aqueous solution of 2-hydroxyethyl methacrylate (HEMA) and 0.1 ml of 10% aqueous ammonium persulfate were added, and, under constant stirring of the mixture with a magnetic stirrer, provided with an aqueous solution of sodium sulfite (2 moles per mole of persulfate). The mixture was slowly mixed at a temperature of 40° C. for 2 hours or at a temperature of 10° C. for 10 h. The polymer was filtered, washed with water and dried at a temperature below 80° C.

EXAMPLE 4

To 1 g of dry polymer prepared in Example 1, 3, 5 ml of ethanol and then 1.6 ml of 6% aqueous solution of HEMA, 0.3 ml of 10% aqueous solution of ammonium persulfate, and finally 0.3 ml of 1 M aqueous solution of sodium sulfite (or 0.3 ml of 0.5 M solution of ascorbinic acid) were added. The mixture was stirred for 10 h at a temperature of 10° C. The polymer was filtered, washed with water and dried at 70° C.

The copolymer of divinylbenzene with buthyl methacrylate prepared in Example 2 was grafted with HEMA in exactly the same manner.

EXAMPLE 5

To 1 g of the wetted with water polymer prepared in Example 1, 1.0 ml of 6% aqueous solution of N-vinylpyrrolidone, and 0.2 ml of 10% aqueous solution of ammonium persulfate were added, and the mixture was stirred for 2 h at a temperature of 40° C. The polymer was filtered, washed with water and dried.

EXAMPLE 6

To 1 g of the polymer wetted with water and prepared in Example 1 2.0 ml of 3% N-vinylpyrrolidone, 0.3 ml of aqueous 10% solution of sodium persulfate and 0.3 ml of sodium sulfite solution were added and the mixture was stirred at 25° C. for 2 h. The polymer was filtered and treated as above.

Polymer Analogous Reactions on the Surface Exposed Double Bonds

EXAMPLE 7

To 1 g of the polymer wetted with water and prepared in Example 2, 2.0 ml of 3% N-acrylamide, 0.3 ml of aqueous 10% solution of sodium persulfate and 0.3 ml of 1 M aqueous solution of sodium sulfite were added and the mixture was stirred at 25° C. for 2 h. The polymer was filtered and treated as above.

EXAMPLE 8

To 6 g of dry polymer prepared in Example 1, 25 ml of acetic anhydride were added, the mixture was cooled to 0° C., slowly provided with 2 ml of aqueous 40% solution of hydrogen peroxide, and stirred at 10–15° C. for 8 h. The polymer was filtered, washed with glacial acetic acid to result in epoxy groups containing material.

2 g of the above epoxy modified polymer, swollen with glacial acetic acid, were provided with 10–15 ml water and 2 drops of concentrated sulfuric acid and heated under stirring 50–70° C. for 3–5 h, thus converting epoxy groups into diol groups. The polymer was filtered, carefully washed with water and dried.

EXAMPLE 9

To 2 g of the epoxy modified (according to Example 7) polymer, swollen with glacial acetic acid, 1 ml of ethylene glycol in 5 ml glacial acetic acid (or 5 ml dry ethyl acetate) were added, provided with 2 drops of concentrated sulfuric acid and heated under stirring for 5–8 h at 50–70° C. This procedure results in the addition of ethylene glycol to the epoxy functional group. The polymer is filtered, washed with water, ethanol and again with water, and dried.

EXAMPLE 10

2 g of the epoxy modified (according to Example 7) polymer, swollen with glacial acetic acid) were carefully washed with dry ethyl acetate and provided with 1 ml of 2-hydroxyethyl amine in 4 ml ethyl acetate. The mixture was stirred at 40° C. for 5 h, which results in the addition of the hydroxyethylamino group to the epoxy group. The polymer was filtered, washed with water, 1 NHCl and again water to neutral pH.

In a separate experiment, diethylamine was taken, instead of 2-hydroxyethyl amine. The product was washed with water 1N HCl and water as described above.

Depositing poly(trifluoroethoxy) phosphazene onto the surface of the polymer (molecular weight $20.10^6$ Dalton)

EXAMPLE 11

The product obtained in Example 9 was dried in vacuum. A solution of 0.3 mg poly(trifluoroethoxy) phosphazene (molecular weight $20.10^6$) in 10 ml ethyl acetate were added quickly to 3 g of the dried polymer and agitated until the whole of the solvent was totally absorbed by beads of the polymer. The material was then dried under reduced pressure and washed with ethanol.

EXAMPLE 12

3 g of dry unmodified polymer prepared in Example 2 were quickly provided with a solution of 1 mg poly (trifluoroethoxy) phosphazene in 10 ml ethyl acetate and then dried from the solvent as described in

EXAMPLE 10

It will be understood that each of the elements described above, or two or more together, may also find a useful application in other types of methods and products differing from the types described above.

While the invention has been illustrated and described as embodied in material for purification of physiological liquids of organism, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A material for purification of physiological fluids of organism, comprising a porous hydrphobic divinylbenzene copolymer which has a size, a shape, and a structure providing removal of toxic compounds from a physiological liquid and which initially has surface exposed vinyl groups in which thereafter the vinyl groups are chemically modified to form different surface exposed functional groups, which are hydrophilic and biocompatible wherein the said modification comprises methods, selected from the group (A) grafting hydrophilic polymer chains by a radical polymerization of 2-hydroxyethyl methacrylate, N-vinylpyrrolidone or N-vinylcaprolactam, (B) oxidation of the vinyl groups to epoxy groups with the subsequent reaction of the epoxy groups with water, ethylene glycol, amines or 2-aminoethanol, and (C) depositing high-molecular weight hemicompatible poly(trifluoroethoxy)phosphazene onto the surface of a polymer.

2. A material as defined in claim 1, wherein said porous hydrphobic divinylbenzene copolymer comprises a copolymer of divinylbenzene with comonomers selected from the group consisting of styrene, ethylstyrene, acrylonitrile, and buthyl methacrylate.

* * * * *